Figure 1:
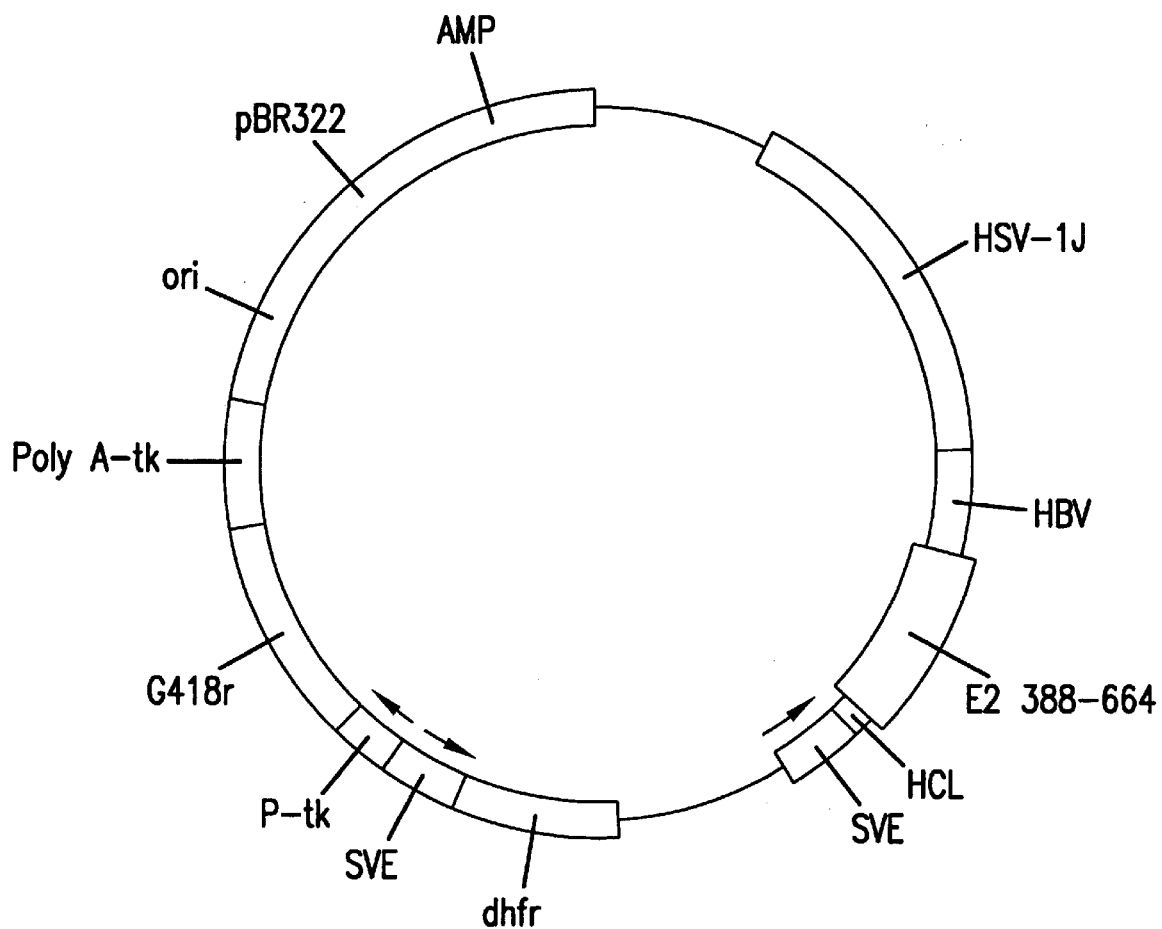

United States Patent [19]
Okasinski et al.

[11] Patent Number: 6,020,122
[45] Date of Patent: *Feb. 1, 2000

[54] HEPATITIS C VIRUS SECOND ENVELOPE (HCV-E2) GLYCOPROTEIN EXPRESSION SYSTEM

[75] Inventors: Gregory F. Okasinski, Wadsworth; Verlyn G. Schaefer, Libertyville; Thomas S. Suhar, Lindenhurst, all of Ill.; Richard R. Lesniewski, Kenosha, Wis.

[73] Assignee: Abbott Laboratories, Abbott Park, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/478,073

[22] Filed: Jun. 7, 1995

[51] Int. Cl.$^7$ ............................................. C12Q 1/70
[52] U.S. Cl. ......................... 435/5; 435/69.1; 435/71.1; 500/350; 424/189.1; 424/228.1
[58] Field of Search ........................... 435/4, 5, 7.1, 69.1, 435/320.1; 424/189.1, 192.1, 228.1, 201.1; 536/23.72

[56] References Cited

U.S. PATENT DOCUMENTS 5,322,769 6/1994 Bolling et al. .

OTHER PUBLICATIONS

Newman et al., 1995, Vaccine Design: The Subunit and Adjuvant Approach, Powell et al., eds., Plenum Press, New York, pp. 1–42.
Graham et al., 1995, New Engl. J. Med. 333:1331–1339.
Prince, 1994, FEMS Microbiol. Rev. 14:273–278.
Lesniewski et al., 1995, J. Med. Virol. 45:415–422.
Yokosuka et al., 1993, Gut supplement:S64–S65.
Harada et al., 1995, J. Gen. Virol. 76:1223–1231.

*Primary Examiner*—Laurie Scheiner
*Assistant Examiner*—Jeffrey S. Parkin
*Attorney, Agent, or Firm*—Cheryl L. Becker; Priscilla Porembski

[57] ABSTRACT

This invention provides a novel mammalian expression system that is capable of generating high levels of expressed hepatitis C virus (HCV) proteins which have previously proved difficult to express due to their non-secretory properties. In particular, the invention provides a plasmid for the expression of the HCV second envelope protein (E2) designated p577. This plasmid encodes a recombinant protein comprising the immunoglobulin signal peptide and amino acids 388–664 of the HCV E2 glycoprotein. This unique expression system produces high levels of HCV proteins that are properly processed, glycosylated, and folded.

4 Claims, 2 Drawing Sheets

```
       SpeI
  1  ACTAGTCGACATGGAGACTGGGCTGCCGCTGGCTTCTCCTGGTCGCTGTGCT
                              XbaI
 52  CAAAGGTGTCCAGTGTCTCGAGGGGTCTAGAAGCAATGAACTTACCG
 99  GGGGAAGTGCCGGCCACACCACGGCTGGGCTTGTTCGTCTCCTTTCACCAGGC
152  GCCAAGCAGAACATCCAACTGATCAACACCAACGGCAGTTGGCACATCAATAG
205  CACGGCCTTGAACTGCAATGAAAGCCTTAACACCGGCTGGTTAGCAGGGCTCT
258  TCTATCACCACAAATTCAACTCTTCAGGTTGTCCTGAGAGGTTGGCCAGCTGC
311  CGACGCCTTACCGATTTTGCCCAGGGCGGGGGTCCTATCAGTTACGCCAACGG
364  AAGCGGCCTCGATGAACGCCCCTACTGCTGGCACTACCCTCCAAGACCTTGTG
417  GCATTGTGCCCGCAAAGAGCGTGTGTGGCCCGGTATATTGCTTCACTCCCAGC
470  CCCGTGGTGGTGGGAACGACCGACAGGTCGGGCGCGCCTACCTACAGCTGGGG
523  TGCAAATGATACGGATGTCTTTGTCCTTAACAACACCAGGCCACCGCTGGGCA
576  ATTGGTTCGGTTGCACCTGGATGAACTCAACTGGATTCACCAAAGTGTGCGGA
629  GCGCCCCCTTGTGTCATCGGAGGGGTGGGCAACAACACCTTGCTCTGCCCCAC
682  TGATTGCTTCCGCAAGCATCCGGAAGCCACATACTCTCGGTGCGGCTCCGGTC
735  CCTGGATTACACCCAGGTGCATGGTCGACTACCCGTATAGGCTTTGGCACTAT
788  CCTTGTACCATCAATTACACCATATTCAAAGTCAGGATGTACGTGGGAGGGGT
841  CGAGCACAGGCTGGAAGCGGCCTGCAACTGGACGCGGGGCGAACGCTGTGATC
                                                 XbaI
894  TGGAAGACAGGGACAGGTCCGAGCTCAGCCCGTGATAATCTAGA
```

FIG.2

```
METGLRWLLLVAVLKGVQC---
LEGSRSNELTGGSAGHTTAGLVRLLSPGAKQNIQLINTNGSWHINSTALNCNESLN
TGWLAGLFYHHKFNSSGCPERLASCRRLTDFAQGGGPISYANGSGLDERPYCWHYP
PRPCGIVPAKSVCGPVYCFTPSPVVVGTTDRSGAPTYSWGANDTDVFVLNNTRPPL
GNWFGCTWMNSTGFTKVCGAPPCVIGGVGNNTLLCPTDCFRKHPEATYSRCGSGPW
ITPRCMVDYPYRLWHYPCTINYTIFKVRMYVGGVEHRLEAACNWTRGERCDLEDRD
RSELSP-
```

FIG.3

SEQUENCE LISTING

```
(1) GENERAL INFORMATION:

(iii) NUMBER OF SEQUENCES: 2

(2) INFORMATION FOR SEQ ID NO:1:

(i) SEQUENCE CHARACTERISTICS:
         (A) LENGTH: 937 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:1:

ACTAGTCGAC ATGGAGACTG GGCTGCGCTG GCTTCTCCTG GTCGCTGTGC TCAAAGGTGT      60

CCAGTGTCTC GAGGGGTCTA GAAGCAATGA ACTTACCGGG GGAAGTGCCG GCCACACCAC     120

GGCTGGGCTT GTTCGTCTCC TTTCACCAGG CGCCAAGCAG AACATCCAAC TGATCAACAC     180

CAACGGCAGT TGGCACATCA ATAGCACGGC CTTGAACTGC AATGAAAGCC TTAACACCGG     240

CTGGTTAGCA GGGCTCTTCT ATCACCACAA ATTCAACTCT TCAGGTTGTC CTGAGAGGTT     300

GGCCAGCTGC CGACGCCTTA CCGATTTTGC CCAGGGCGGG GGTCCTATCA GTTACGCCAA     360

CGGAAGCGGC CTCGATGAAC GCCCCTACTG CTGGCACTAC CCTCCAAGAC CTTGTGGCAT     420

TGTGCCCGCA AAGAGCGTGT GTGGCCCGGT ATATTGCTTC ACTCCCAGCC CCGTGGTGGT     480
```

```
GGGAACGACC GACAGGTCGG GCGCGCCTAC CTACAGCTGG GGTGCAAATG ATACGGATGT        540

CTTTGTCCTT AACAACACCA GGCCACCGCT GGGCAATTGG TTCGGTTGCA CCTGGATGAA        600

CTCAACTGGA TTCACCAAAG TGTGCGGAGC GCCCCCTTGT GTCATCGGAG GGTGGGCAA         660

CAACACCTTG CTCTGCCCCA CTGATTGCTT CCGCAAGCAT CCGGAAGCCA CATACTCTCG        720

GTGCGGCTCC GGTCCCTGGA TTACACCCAG GTGCATGGTC GACTACCCGT ATAGGCTTTG        780

GCACTATCCT TGTACCATCA ATTACACCAT ATTCAAAGTC AGGATGTACG TGGGAGGGGT        840

CGAGCACAGG CTGGAAGCGG CCTGCAACTG GACGCGGGGC GAACGCTGTG ATCTGGAAGA        900

CAGGGACAGG TCCGAGCTCA GCCCGTGATA ATCTAGA                                937
```

(2) INFORMATION FOR SEQ ID NO:2:

(i) SEQUENCE CHARACTERISTICS:
        (A) LENGTH: 305 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Glu Thr Gly Leu Arg Trp Leu Leu Leu Val Ala Val Leu Lys Gly
1               5                   10                  15

Val Gln Cys Leu Glu Gly Ser Arg Ser Asn Glu Leu Thr Gly Gly Ser
            20                  25                  30

Ala Gly His Thr Thr Ala Gly Leu Val Arg Leu Leu Ser Pro Gly Ala
        35                  40                  45

Lys Gln Asn Ile Gln Leu Ile Asn Thr Asn Gly Ser Trp His Ile Asn
    50                  55                  60

Ser Thr Ala Leu Asn Cys Asn Glu Ser Leu Asn Thr Gly Trp Leu Ala
65                  70                  75                  80

Gly Leu Phe Tyr His His Lys Phe Asn Ser Ser Gly Cys Pro Glu Arg
                85                  90                  95

Leu Ala Ser Cys Arg Arg Leu Thr Asp Phe Ala Gln Gly Gly Gly Pro
            100                 105                 110

Ile Ser Tyr Ala Asn Gly Ser Gly Leu Asp Glu Arg Pro Tyr Cys Trp
        115                 120                 125

His Tyr Pro Pro Arg Pro Cys Gly Ile Val Pro Ala Lys Ser Val Cys
    130                 135                 140

Gly Pro Val Tyr Cys Phe Thr Pro Ser Pro Val Val Gly Thr Thr
145                 150                 155                 160

Asp Arg Ser Gly Ala Pro Thr Tyr Ser Trp Gly Ala Asn Asp Thr Asp
                165                 170                 175

Val Phe Val Leu Asn Asn Thr Arg Pro Pro Leu Gly Asn Trp Phe Gly
            180                 185                 190

Cys Thr Trp Met Asn Ser Thr Gly Phe Thr Lys Val Cys Gly Ala Pro
        195                 200                 205

Pro Cys Val Ile Gly Gly Val Gly Asn Asn Thr Leu Leu Cys Pro Thr
    210                 215                 220

Asp Cys Phe Arg Lys His Pro Glu Ala Thr Tyr Ser Arg Cys Gly Ser
225                 230                 235                 240

Gly Pro Trp Ile Thr Pro Arg Cys Met Val Asp Tyr Pro Tyr Arg Leu
                245                 250                 255

Trp His Tyr Pro Cys Thr Ile Asn Tyr Thr Ile Phe Lys Val Arg Met
            260                 265                 270
```

-continued

```
Tyr Val Gly Gly Val Glu His Arg Leu Glu Ala Ala Cys Asn Trp Thr
        275                 280                 285

Arg Gly Glu Arg Cys Asp Leu Glu Asp Arg Asp Arg Ser Glu Leu Ser
        290                 295                 300

Pro
305
```

HEPATITIS C VIRUS SECOND ENVELOPE (HCV-E2) GLYCOPROTEIN EXPRESSION SYSTEM

RELATED APPLICATIONS

This application is related to pending U.S. patent application Ser. No. 08/188,281, filed Jan. 28, 1994, entitled "Mammalian Expression Systems for Hepatitis C Virus Envelope Genes" and to pending U.S. patent application Ser. No. 08/144,099, filed Oct. 28, 1993, entitled "Mammalian Expression Systems for Hepatitis C Virus", which is a continuation of U.S. Ser. No. 07/830,024, both of which enjoy common ownership and are incorporated herein by reference.

BACKGROUND OF THE INVENTION

This invention relates generally to a mammalian expression system, and more particularly, relates to a mammalian expression system capable of generating recombinant proteins not heretofore generated at such high levels due to the non-secretor nature of the gene. The recombinant proteins are expressed in culture medium as well as in mammalian cells.

The introduction of the first-generation hepatitis C virus (HCV) enzyme immunoassays (EIAs) (HCV 1.0 EIAs) as screening assays in 1989 and second-generation HCV EIAs in 1992 (HCV 2.0 EIAs) has dramatically reduced the incidence of post-transfusion HCV (PT-HCV) infection in those countries where routine screening of donated blood products is performed. Antibodies to HCV are detected using recombinant proteins derived from the core, NS3 (viral protease) and NS4 (function unknown) genes of the virus. HCV third-generation EIAs (HCV 3.0 EIAs) which include an additional antigen from the NS5 region (containing the viral polymerase and a second unknown function) now are available and in use in several countries. HCV envelope antigens have not been used in these assays.

Difficulties in the expression and purification of the putative HCV viral envelope proteins (E1, E2) have prevented detailed research and possible incorporation of these proteins as targets in blood screening assays. There may be several reasons for the difficulties encountered in getting a cell to synthesize a heterologous protein and subsequently, to detect and recover the protein. For example, the heterologous gene may not be efficiently transcribed into messenger RNA (mRNA). Also, the mRNA may be unstable and degrade prior to translation into the protein. In addition, the ribosome binding site (RBS) present on the mRNA may only poorly initiate translation. The heterologous protein produced may be unstable in the cell or it may be toxic to the cell. If no antibodies to the protein are available or if there is no other way to assay for the protein, it may be difficult to detect the synthesized protein. Lastly, even if the protein is produced, it may be difficult to purify.

Fusion systems provide a means of solving many of the aforementioned problems. The "carrier" portion of the hybrid gene, typically found on the 5' end of the gene, provides the regulatory regions for transcription and translation as well as providing the genetic code for a peptide which facilitates detection (Shuman et al., *J. Biol. Chem.* 255:168 [1980]) and/or purification (Moks et al., *Bio/Technology* 5:379 [1987]). Frequently, potential proteolytic cleavage sites are engineered into the fusion protein to allow for the removal of the homologous peptide portion (de Geus et al., *Nucleic Acids Res.* 15:3743 [1987]; Nambiar et al., *Eur. J. Biochem.* 163:67 [1987]; Imai et al., *J. Biochem.* 100:425 [1986]).

When selecting a carrier gene for a fusion system, in addition to detectability and ease of purification, it would be extremely advantageous to start with a highly expressed gene. Expression is the result of not only efficient transcription and translation but also protein stability and benignity (the protein must not harm or inhibit the cell host). Such expression is advantageous because it can enable the production of such fusion proteins for use in assays. In genes where such expression is not possible, it would be advantageous to provide a system whereby a non-secretor gene can secrete, or express, protein in sufficient amounts to be useful in commercial assays or for other purposes such as for vaccine production.

SUMMARY OF THE INVENTION

This invention provides a novel mammalian expression system that is capable of generating high levels of expressed proteins which proteins heretofore have been difficult to express due to the non-secretor nature of the gene. In particular, the invention provides a plasmid for the expression of the HCV E2 antigen. This unique expression systems allow for the production of high levels of HCV proteins, allowing to the proper processing, glycosylation and conformation (folding) of the viral protein(s) in the system. In particular, the present invention provides the plasmid 577. HCV E2 fusion protein, expressed from plasmid 577 in the mammalian expression system of the invention, can be recovered extracelluarly as well as intracellularly.

BRIEF DESCRIPTION OF THE DRAWINGS

FIG. 1 is a graphic representation of plasmid 577.

FIG. 2 is the DNA sequence of HCV E2 antigen expression cassette.

FIG. 3 (labelled translation figure) shows a conceptual translation of the HCV E2 gene and the signal protease cleavage site wherein " - - - " denotes a signal peptidease cleavage site.

DETAILED DESCRIPTION OF THE INVENTION

The present invention provides ways to produce glycosylated HCV E2 fusion proteins expressed in mammalian expression systems. These glycosylated proteins have utility for a variety of applications, including, for example, assay systems for screening and prognostic applications, and as vaccine preparations. These HCV viral envelope proteins expressed in mammalian cells also allow for inhibitor studies including elucidation of specific viral attachment sites or sequences and/or viral receptors on susceptible cell types, for example, liver cells and the like.

The procurement of specific expression clones developed as described herein in mammalian expression systems provides antigens for diagnostic assays which can aid in determining the stage of HCV infection, such as, for example, acute versus on-going or persistent infections, and/or recent infection versus past exposure. These specific expression clones also provide prognostic markers for resolution of disease such as to distinguish resolution of disease from chronic hepatitis caused by HCV. It is contemplated that earlier seroconversion to glycosylated structural antigens may be detectable by using proteins produced in these mammalian expression systems. Antibodies, both monoclonal and polyclonal, also may be produced from the proteins derived from these mammalian expression systems which then in turn may be used for diagnostic, prognostic and therapeutic applications.

Proteins produced from these mammalian expression systems, as well as reagents produced from these proteins, can be provided in the form of a kit with one or more containers such as vials or bottles, with each container containing a separate reagent such as a monoclonal antibody, or a cocktail of monoclonal antibodies, or a recombinant protein, packaged as test kits for convenience in performing assays. Other aspects of the present invention include a recombinant protein comprising an HCV epitope attached to a solid phase and an antibody to an HCV epitope attached to a solid phase. Also included are methods for producing a recombinant protein containing an HCV epitope by incubating host cells transformed with a mammalian expression vector containing a sequence encoding a polypeptide containing an HCV epitope under conditions which allow expression of the polypeptide, and a polypeptide containing an HCV epitope produced by this method.

The present invention provides assays which utilize the recombinant proteins provided by the invention, as well as the antibodies described herein in various formats, any of which may employ a signal generating compound which generates a measurable signal in the assay. Assays which do not utilize signal generating compounds to provide a means of detection also are provided. All of the assays described generally detect either antigen or antibody, or both, and include mixing a test sample with at least one reagent provided herein to form at least one antigen/antibody complex and detecting the presence of the complex. These assays are described in detail herein.

Vaccines for treatment of HCV infection comprising an immunogenic peptide obtained from a mammalian expression system containing envelope genes from HCV as described herein are included in the present invention. Also included in the present invention is a method for producing antibodies to HCV comprising administering to an individual an isolated immunogenic polypeptide containing an HCV epitope in an amount sufficient to produce an immune response in the inoculated individual.

The term "test sample" refers to a component of an individual's body which is the source of the antibodies of interest. These components are well known in the art and include biological samples which can be tested by the methods described herein. Examples of test samples include human and animal body fluids such as whole blood, serum, plasma, cerebrospinal fluid, urine, lymph fluids, and various external sections of the respiratory, intestinal and genitourinary tracts, tears, saliva, milk, white blood cells, myelomas and the like, biological fluids such as cell culture supernatants, fixed tissue specimens and fixed cell specimens.

After preparing the recombinant proteins as described by the present invention, these recombinant proteins can be used to develop unique assays as described herein to detect either the presence of antigen or antibody to HCV. These compositions also can be used to develop monoclonal and/or polyclonal antibodies with a specific recombinant protein which specifically binds to the immunological epitope of HCV. Also, it is contemplated that recombinant proteins made by the method described herein can be used to develop vaccines by following methods known in the art.

Typically, such vaccines are prepared as injectables, either as liquid solutions or suspensions; solid forms suitable for solution in or suspension in liquid prior to injection also may be prepared. The preparation may be emulsified. or the protein may be encapsulated in liposomes. The active immunogenic ingredients often are mixed with pharmacologically acceptable excipients which are compatible with the active ingredient. Suitable excipients include but are not limited to water, saline, dextrose, glycerol, ethanol and the like; combinations of these excipients in various amounts also may be used. The vaccine also may contain small amounts of auxiliary substances such as wetting or emulsifying reagents, pH buffering agents, and/or adjuvants which enhance the effectiveness of the vaccine. For example, such adjuvants can include aluminum hydroxide, N-acetyl-muramyl-L-threonyl-D-isoglutamine (thr-DMP), N-acetyl-nornuramyl-L-alanyl-D-isoglutamine (CGP 11687, also referred to as nor-MPD), N-acetylmuramyul-L-alanyl-D-isoglutaminyl-L-alanine-2-(1'2'-dipalmitoyl-sn-glycero-3-hydroxphosphoryloxy)-ethylamine (CGP19835A, also referred to as MTP-PE), and RIBI (MPL+TDM+CWS) in a 2% squalene/Tween-80® emulsion. The effectiveness of an adjuvant may be determined by measuring the amount of antibodies directed against an immunogenic polypeptide containing an HCV antigenic sequence resulting from administration of this polypeptide in vaccines which also are comprised of the various adjuvants.

The vaccines usually are administered by intraveneous or intramuscular injection. Additional formulations which are suitable for other modes of administration include suppositories and, in some cases, oral formulations. For suppositories, traditional binders and carriers may include but are not limited to polyalkylene glycols or triglycerides. Such suppositories may be formed from mixtures containing the active ingredient in the range of about 0.5% to about 10%, preferably, about 1% to about 2%. Oral formulation include such normally employed excipients as, for example pharmaceutical grades of mannitol, lactose, starch, magnesium stearate, sodium saccharine, cellulose, magnesium carbonate and the like. These compositions may take the form of solutions, suspensions, tablets, pills, capsules, sustained release formulations or powders and contain about 10% to about 95% of active ingredient, preferably about 25% to about 70%.

The proteins used in the vaccine may be formulated into the vaccine as neutral or salt forms. Pharmaceutically acceptable salts such as acid addition salts (formed with free amino groups of the peptide) and which are formed with inorganic acids such as hydrochloric or phosphoric acids, or such organic acids such as acetic, oxalic, tartaric, maleic, and others known to those skilled in the art. Salts formed with the free carboxyl groups also may be derived from inorganic bases such as sodium, potassium, ammonium, calcium or ferric hydroxides and the like, and such organic bases such as isopropylamine, trimethylamine, 2-ethylamino ethanol, histidine procaine, and others known to those skilled in the art.

Vaccines are administered in a way compatible with the dosage formulation, and in such amounts as will be prophylactically and/or therapeutically effective. The quantity to be administered generally is in the range of about 5 micrograms to about 250 micrograms of antigen per dose, and depends upon the subject to be dosed, the capacity of the subject's immune system to synthesize antibodies, and the degree of protection sought. Precise amounts of active ingredient required to be administered also may depend upon the judgment of the practitioner and may be unique to each subject. The vaccine may be given in a single or multiple dose schedule. A multiple dose is one in which a primary course of vaccination may be with one to ten separate doses, followed by other doses given at subsequent time intervals required to maintain and/or to reenforce the immune response, for example, at one to four months for a second dose, and if required by the individual, a subsequent dose(s) after several months. The dosage regimen also will be determined, at least in part, by the need of the individual, and be dependent upon the practitioner's judgment. It is contemplated that the vaccine containing the immunogenic HCV envelope antigen(s) may be administered in conjunction with other immunoregulatory agents, for example, with immune globulins.

The expression of a gene coding for a protein of interest using a DNA cloning vehicle which includes (a) expression control regions, (b) a region coding for the rabbit immunoglobulin heavy chain gamma secretion signal sequence, (c) bacterial enzyme for selection in eukaryotic cells, (d) an amplification system suitable for enhanced expresision in eukaryotic cells, and (e) a region coding for the protein of interest generally is described herein. The cloning vehicles described herein are capable of expressing fusion proteins; that is, immunoglobulin signal peptides sequences and adjacent immunoglobulin coding sequences fused to heterologous protein at commercially useful levels. FIG. 1 shows generically the features of a plasmid useful for production of fusion proteins used in the methods of this invention. The plasmid in FIG. 1 is disclosed as a series of assembled fragments with sections 1 to 13. The accession numbers of the sections refer to Genbank® accession numbers. The plasmid includes a control region (described hereinbelow), followed by a gene encoding an immunoglobulin signal peptide and adjacent immunoglobilin coding sequences which are linked to a gene coding for a heterologous protein of interest. Please note that slight sequence variations may occur and may have occurred when constructing the plasmid.

TABLE 1

Plasmid Figure Legend Construction
Plasmid 577, 10,186 base pairs double stranded DNA

| SECTION | DESCRIPTION |
|---|---|
| 1 | (NT 4361-2067 OF PBR322 ACCESSION J02224) |
| 2 | (NT 2249-1624 HSV-1 ACCESSION J02224 NT) |
| 3 | (NT 2518-1519 Tn5 ACCESSION NOS U00004 L19385) |
| 4 | (NT 460-210 HSV-1 ACCESSION J02224) |
| 5 | (NT 272-1, 5243-5173 SV40) |
| 6 | (NT 1-701 MOUSE DHFR ACCESSION L26316) |
| 7 | (NT 4714-4100 SV40 ACCESSION V08380) |
| 8 | (NT 272-1, 5243-5173 5V40) |
| 9 | (NT 1-77 DNA Sequence Figure SYNTHETIC DNA RABBITT IgG HEAVY CHAIN LEADER (HCL)) |
| 10 | (NT 78-938 DNA Sequence Figure HCV E2 antigen PCR product) |
| 11 | (HBV ENHANCER NT 2373-2811 ACCESSION NO. X02763 WITH G AT NT. 2976 AND T AT NT. 2654) |
| 12 | (NT 3688-5468 HSV1 ACCESSION NO. NT 3687-5468) |
| 13 | (NT 2536-1785 SV40 ACCESSION V08380) |

Insertion of heterologous genes into a plasmid as described in FIG. 1 can be accomplished with various techniques known to those in the art. These fusion proteins can be utilized in various assay formats as capture reagents or protein binders in numerous ways. After preparing the recombinant proteins as described herein, the recombinant proteins can be used to develop unique assays as described herein to detect either the presence of a specific binding member of a specific binding pair. These recombinant proteins also can be used to develop monoclonal and/or polyclonal antibodies with a specific recombinant protein or synthetic peptide which specifically binds to the specific binding member of a specific binding pair. The fusion proteins described herein also can be used as the active ingredient of a vaccine.

Vaccine Preparation

Vaccines may be prepared from one or more immunogenic polypeptides derived from nucleic acid sequences of interest or from the genome of interest to which they correspond. Vaccines may comprise recombinant polypeptides containing epitope(s) of interest. These polypeptides may be expressed in bacteria, yeast or mammalian cells, or alternatively may be isolated from viral preparations. It also is anticipated that various structural proteins may contain epitopes of interest which give rise to protective anti-epitope antibodies. Synthetic peptides therefore also can be utilized when preparing these vaccines. Thus, polypeptides containing at least one epitope of interest may be used, either singly or in combinations, in these vaccines. It also is contemplated that nonstructural proteins as well as structural proteins may provide protection against viral pathogenicity, even if they do not cause the production of neutralizing antibodies.

Considering the above, multivalent vaccines may comprise one or more structural proteins, and/or one or more nonstructural proteins. These vaccines may be comprised of, for example, recombinant polypeptides expressed by the plasmid of the invention and/or polypeptides isolated from the virions and/or synthetic peptides. These immunogenic epitopes can be used in combinations, i.e., as a mixture of recombinant proteins, synthetic peptides and/or polypeptides isolated from the virion; these may be administered at the same or different time. Additionally, it may be possible to use inactivated viruses in vaccines. Such inactivation may be be preparation of viral lysates, or by other means known in the art to cause inactivation of hepatitis-like viruses, for example, treatment with organic solvents or detergents, or treatment with formalin. Attenuated viral strain preparation also is disclosed in the present invention. It is contemplated that some of the proteins may cross-react with other known viruses, and thus that shared epitopes may exist between the virus of interest and other viruses which would then give rise to protective antibodies against one or more of the disorders caused by these pathogenic agents. It is contemplated that it may be possible to design multiple purpose vaccines based upon this belief.

The preparation of vaccines which contain at least one immunogenic peptide as an active ingredient is known to one skilled in the art. Typically, such vaccines are prepared as injectables, either as liquid solutions or suspensions; solid forms suitable for solution in or suspension in liquid prior to injection also may be prepared. The preparation may be emulsified or the protein may be encapsulated in liposomes. The active immunogenic ingredients often are mixed with pharmacologically acceptable excipients which are compatible with the active ingredient. Suitable excipients include but are not limited to water, saline, dextrose, glycerol, ethanol and the like; combinations of these excipients in various amounts also may be used. The vaccine also may contain small amounts of auxiliary substances such as wetting or emulsifying reagents, pH buffering agents, and/or adjuvants which enhance the effectiveness of the vaccine. For example, such adjuvants can include aluminum hydroxide, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), and REBI (MPL+TDM+CWS) in a 2% squalene/Tween-80® emulsion. The effectiveness of an adjuvant may be determined by measuring the amount of antibodies directed against an immunogenic polypeptide containing an antigenic sequence produced by the plasmid disclosed herein, resulting from administration of this polypeptide in vaccines which also are comprised of the various adjuvants.

The vaccines usually are administered by intravenous or intramuscular injection. Additional formulations which are suitable for other modes of administration include suppositories and, in some cases, oral formulations. For suppositories, traditional binders and carriers may include but are not limited to polyalkylene glycols or triglycerides. Such suppositories may be formed from mixtures containing the active ingredient in the range of about 0.5% to about 10%, preferably, about 1% to about 2%. Oral formulation include such normally employed excipients as, for example pharmaceutical grades of mannitol, lactose, starch, magnesium stearate, sodium saccharine, cellulose, magnesium carbonate and the like. These compositions may take the form of solutions, suspensions, tablets, pills, capsules, sustained release formulations or powders and contain about 10% to about 95% of active ingredient, preferably about 25% to about 70%.

The proteins used in the vaccine may be formulated into the vaccine as neutral or salt forms. Pharmaceutically acceptable salts such as acid addition salts (formed with free amino groups of the peptide) and which are formed with inorganic acids such as hydrochloric or phosphoric acids, or such organic acids such as acetic, oxalic, tartaric, maleic, and others known to those skilled in the art. Salts formed with the free carboxyl groups also may be derived from inorganic bases such as sodium, potassium, ammonium, calcium or ferric hydroxides and the like, and such organic bases such as isopropylamine, trimethylamine, 2-ethylamino ethanol, histidine procaine, and others known to those skilled in the art.

Vaccines are administered in a way compatible with the dosage formulation, and in such amounts as will be prophylactically and/or therapeutically effective. The quantity to be administered generally is in the range of about 5 micrograms to about 250 micrograms of antigen per dose, and depends upon the subject to be dosed, the capacity of the subject's immune system to synthesize antibodies, and the degree of protection sought. Precise amounts of active ingredient required to be administered also may depend upon the judgment of the practitioner and may be unique to each subject. The vaccine may be given in a single or multiple dose schedule. A multiple dose is one in which a primary course of vaccination may be with one to ten separate doses, followed by other doses given at subsequent time intervals required to maintain and/or to reinforce the immune response, for example, at one to four months for a second dose, and if required by the individual, a subsequent dose(s) after several months. The dosage regimen also will be determined, at least in part, by the need of the individual, and be dependent upon the practitioner's judgment. It is contemplated that the vaccine containing the immunogenic antigen(s) prepared as described herein may be administered in conjunction with other immunoregulatory agents, for example, with immune globulins.

Assay Formats

It is contemplated that the reagent employed for the assay can be provided in the form of a kit with one or more containers such as vials or bottles, with each container containing a separate reagent such as a monoclonal antibody, or a cocktail of monoclonal antibodies, or a recombinant protein employed in the assay.

"Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances, haptens, antibodies, and combinations thereof. As a member of a specific binding pair, the analyte can be detected by means of naturally occurring specific binding partners (pairs) such as the use of intrinsic factor protein as a member of a specific binding pair for the determination of Vitamin B12, the use of folate-binding protein to determine folic acid, or the use of a lectin as a member of a specific binding pair for the determination of a carbohydrate. The analyte can include a protein, a peptide, an amino acid, a hormone, a steroid, a vitamin, a drug including those administered for therapeutic purposes as well as those administered for illicit purposes, a bacterium, a virus, and metabolites of or antibodies to any of the above substances. The details for the preparation of such antibodies and the suitability for use as specific binding members are well known to those skilled in the art. Viruses which can be tested include hepatitis-causing viruses (for example, hepatitis A virus, hepatitis B virus, hepatitis C virus, hepatitis delta, and hepatitis E virus, and hepatitis GB viruses), human immunodeficiency viruses (such as HIV-1, HIV-2), the HTLV-I and HTLV-II viruses, and the like.

The present invention provides assays which utilize specific binding members. A "specific binding member," as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal, and complexes thereof, including those formed by recombinant DNA molecules. The term "hapten", as used herein, refers to a partial antigen or non-protein binding member which is capable of binding to an antibody, but which is not capable of eliciting antibody formation unless coupled to a carrier protein.

A "capture reagent", as used herein, refers to an unlabeled specific binding member which is specific either for the analyte as in a sandwich assay, for the indicator reagent or analyte as in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample.

"Indicator Reagents" may be used in the various assay formats described herein. The "indicator reagent" comprises a "signal generating compound" (label) which is capable of generating a measurable signal detectable by external means conjugated (attached) to a specific binding member for the analyte. "Specific binding member" as used herein means a member of a specific binding pair. That is, two different molecules where one of the molecules through chemical or physical means specifically binds to the second molecule. In addition to being an antibody member of a specific binding pair for the analyte, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to the analyte as in a sandwich assay, to the capture reagent as in a competitive assay, or to the ancillary specific binding member as in an indirect assay.

The various "signal generating compounds" (labels) contemplated include chromogens, catalysts such as enzymes, luminescent compounds such as fluorescein and rhodamine, chemiluminescent compounds, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

"Solid phases" ("solid supports") are known to those in the art and include the walls of wells of a reaction tray, test tubes, polystyrene beads, magnetic beads, nitrocellulose strips, membranes, microparticles such as latex particles, and others. The "solid phase" is not critical and can be selected by one skilled in the art. Thus, latex particles, microparticles, magnetic or non-magnetic beads, membranes, plastic tubes, walls of microtiter wells, glass or silicon chips and sheep red blood cells are all suitable examples. Suitable methods for immobilizing peptides on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, and other configurations known to those of ordinary skill in the art.

It is contemplated and within the scope of the invention that the solid phase also can comprise any suitable porous material with sufficient porosity to allow access by detection antibodies and a suitable surface affinity to bind antigens. Microporous structures are generally preferred, but materials with gel structure in the hydrated state may be used as well. Such useful solid supports include:

natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto or bonded or laminated to appropriate inert carriers, such as paper, glass, plastic films, or fabrics.

The porous structure of nitrocellulose has excellent absorption and adsorption qualities for a wide variety of reagents including monoclonal antibodies. Nylon also possesses similar characteristics and also is suitable. It is contemplated that such porous solid supports described hereinabove are preferably in the form of sheets of thickness from about 0.01 to 0.5 mm, preferably about 0.1 mm. The pore size may vary within wide limits, and is preferably from about 0.025 to 15 microns, especially from about 0.15 to 15 microns. The surfaces of such supports may be activated by chemical processes which cause covalent linkage of the antigen or antibody to the support. The irreversible binding of the antigen or antibody is obtained, however, in general, by adsorption on the porous material by poorly understood hydrophobic forces. Suitable solid supports also are described in U.S. patent application Ser. No. 227,272.

The term "test sample" includes biological samples which can be tested by the methods of the present invention described herein and include human and animal body fluids such as whole blood, serum, plasma, cerebrospinal fluid, urine, lymph fluids, and various external secretions of the respiratory, intestinal and genitorurinary tracts, tears, saliva, milk, white blood cells, myelomas and the like, biological fluids such as cell culture supernatants, fixed tissue specimens and fixed cell specimens. Any substance which can be adapted for testing with the recombinant proteins described herein and assay formats of the present invention are contemplated to be within the scope of the present invention.

Other embodiments which utilize various other solid phases also are contemplated and are within the scope of this invention. For example, ion capture procedures for immobilizing an immobilizable reaction complex with a negatively charged polymer, described in co-pending U.S. patent application Ser. No. 150,278 corresponding to EP publication 0326100, and U.S. patent application Ser. No. 375,029 (EP publication no. 0406473) both of which enjoy common ownership and are incorporated herein by reference, can be employed according to the present invention to effect a fast solution-phase immunochemical reaction. An immobilizable immune complex is separated from the rest of the reaction mixture by ionic interactions between the negatively charged poly-anion/immune complex and the previously treated, positively charged porous matrix and detected by using various signal generating systems previously described, including those described in chemiluminescent signal measurements as described in co-pending U.S. patent application Ser. No. 921,979 corresponding to EPO Publication No. 0 273,115, which enjoys common ownership and which is incorporated herein by reference.

Also, the methods of the present invention can be adapted for use in systems which utilize microparticle technology including in automated and semi-automated systems wherein the solid phase comprises a microparticle. Such systems include those described in pending U.S. patent applications Ser. No. 425,651 and 425,643, which correspond to published EPO applications Nos. EP 0 425 633 and EP 0 424 634, respectively, which are incorporated herein by reference.

The use of scanning probe microscopy (SPM) for immunoassays also is a technology to which the recombinant proteins of the present invention or monoclonal antibodies produced from these recombinant proteins are easily adaptable. In scanning probe microscopy, in particular in atomic force microscopy, the capture phase, for example, either a recombinant protein produced by the novel plasmid described herein or a monoclonal antibody produced therefrom, is adhered to a solid phase, the test sample is contacted to the solid phase for a time and under conditions sufficient for a reaction between the two to occur, and a scanning probe microscope is utilized to detect antigen/antibody complexes which may be present on the surface of the solid phase. The use of scanning tunnelling microscopy eliminates the need for labels which normally must be utilized in many immunoassay systems to detect antigen/antibody complexes.

In an assay format to detect the presence of antibody against a specific analyte (for example, an infectious agent such as a virus) in a human test sample, the human test sample is contacted and incubated with a solid phase coated with at least one recombinant protein (polypeptide). If antibodies are present in the test sample, they will form a complex with the antigenic polypeptide and become affixed to the solid phase. After the complex has formed, unbound materials and reagents are removed by washing the solid phase. The complex is reacted with an indicator reagent and allowed to incubate for a time and under conditions for second complexes to form. The presence of antibody in the test sample to the recombinant polypeptide(s) is determined by detecting the measurable signal generated. Signal generated above a cut-off value is indicative of antibody to the analyte present in the test sample. With many indicator reagents, such as enzymes, the amount of antibody present is proportional to the signal generated. Depending upon the type of test sample, it may be diluted with a suitable buffer reagent, concentrated, or contacted with the solid phase without any manipulation ("neat"). For example, it usually is preferred to test serum or plasma samples which previously have been diluted, or concentrate specimens such as urine, in order to determine the presence and/or amount of antibody present.

A sandwich assay is provided in still another embodiment. This method comprises contacting a test sample with a solid phase to which at least one recombinant antigen provided herein or a combination including at least one recombinant antigen provided herein are bound, to form a mixture. This mixture is incubated for a time and under conditions sufficient to allow antigen/antibody complexes to form. These complexes then are contacted with an indicator reagent comprising antigen(s) previously conjugated to a signal generating compound, to form a second mixture. This second mixture is incubated for a time and under conditions sufficient for antigen/antibody/indicator reagent complexes to form. The presence of the antigen/antibody/indicator reagent complexes is determined by detecting the measurable signal generated. In this assay, a first antigen which can be a recombinant antigen provided herein specific to the antibody to be detected is immobilized on a solid phase, a test sample suspected of containing the antibody is added to the solid phase, and a second antigen which can be a recombinant antigen of the invention having a label affixed thereto then is contacted with the solid phase. Thus, two recombinant antigens which are specific to a single binding pair member are used in one assay as a capture phase and a part of the indicator reagent. These antigens are the same and may be made in different, e.g., heterologous, sources. These sources could be bacterial and yeast, for example. It also is within the scope of the present invention that one recombinant antigen provided herein could be used as the capture reagent or as part of the indicator reagent, and the other antigen in this assay could be a synthetic peptide, or viral lysate, or obtained from other antigenic sources known to the routineer. Further, the use of biotin and antibiotin, biotin and avidin, biotin and streptavidin, and the like, may be used to enhance the generated signal in such assays.

In addition, more than one recombinant protein can be used in the assay format just described to test for the presence of antibody against a specific infectious agent by utilizing fusion proteins prepared as described herein against various antigenic epitopes of the viral genome of the infectious agent under study. Thus, it may be preferred to use recombinant polypeptides which contain epitopes within a specific viral antigenic region as well as epitopes from other antigenic regions from the viral genome to provide assays which have increased sensitivity any perhaps greater specificity than using a polypeptide from one epitope. Such an assay can be utilized as a confirmatory assay. In this particular assay format, a known amount of test sample is contacted with (a) known amount(s) of at least one solid support coated with at least one recombinant protein for a time and under conditions sufficient to form recombinant protein/antibody complexes. The complexes are contacted with known amount(s) of appropriate indicator reagent(s)s for a time and under suitable conditions for a reaction to occur, wherein the resultant signal generated is compared to a negative test sample in order to determine the presence of antibody to the analyte in the test sample. It further is contemplated that, when using certain solid phases such as microparticles, each recombinant protein utilized in the assay can be attached to a separate microparticle, and a mixture of these microparticles made by combining the various coated microparticles, which can be optimized for each assay.

Variations to the above-described assay formats include the incorporation of recombinant proteins produced by the plasmid descibed herein of different analytes attached to the same or to different solid phases for the detection of the presence of antibody to either analyte (for example, recombinant proteins specific for certain antigenic regions of HIV-1 coated on the same or different solid phase with recombinant proteins specific for certain antigenic region(s) of HIV-2, to detect the presence of either (or both) HIV-1 or HIV-2).

In yet another assay format, recombinant proteins produced from the plasmid described herein containing antigenic epitopes are useful in competitive assays such as neutralization assays. To perform a neutralization assay, a recombinant polypeptide representing epitopes of an antigenic region of an infectious agent such as a virus, is solubilized and mixed with a sample diluent to a final concentration of between 0.5 to 50.0 µg/ml. A known amount of test sample (preferably 10 µl), either diluted or non-diluted, is added to a reaction well, followed by 400 µl of the sample diluent containing the recombinant polypeptide. If desired, the mixture may be preincubated for approximately 15 minutes to two hours. A solid phase coated with the recombinant protein described herein then is added to the reaction well, and incubated for one hour at approximately 40° C. After washing, a known amount of an indicator reagent, for example, 200 µl of a peroxide labelled goat anti-human IgG in a conjugate diluent is added and incubated for one hour at 40° C. After washing and when using an enzyme conjugate such as described, an enzyme substrate, for example, OPD substrate, is added and incubated at room temperature for thirty minutes. The reaction is terminated by adding a stopping reagent such as 1N sulfuric acid to the reaction well. Absorbance is read at 492 nm. Test samples which contain antibody to the specific polypeptide generate a reduced signal caused by the competitive binding of the peptides to these antibodies in solution. The percentage of competitive binding may be calculated by comparing absorbance value of the sample in the presence of recombinant polypeptide to the absorbance value of the sample assayed in the absence of a recombinant polypeptide at the same dilution. Thus, the difference in the signals generated between the sample in the presence of recombinant protein and the sample in the absence of recombinant protein is the measurement used to determine the presence or absence of antibody.

Other neutralization assays are contemplated. These include competititve assays to detect the amount, if any, of an antigen analyte in a test sample. The assay comprises the steps of contacting a test sample with a known amount of analyte (in this instance, the recombinant antigen of the invention) having attached to it a signal generating compound and a solid phase to which has been attached an anti-analyte antibody. This resultant mixture is incubated for a time and under conditions sufficient to form either solid phaselanalyte complexes or solid phase/recombinant antigen complexes. The signal is triggered through means known in the art. Test samples which contain antibody to the specific polypeptide generate a reduced signal caused by the competitive binding of the antibody on the solid phase to the antigens in solution. The percentage of competitive binding may be calculated by comparing absorbance value of the sample in the presence of recombinant polypeptide to the absorbance value of the sample assayed in the absence of a recombinant polypeptide at the same dilution. Thus, the difference in the signals generated between the sample in the presence of recombinant protein and the sample in the absence of recombinant protein is the measurement used to determine the presence or absence of antibody.

In another assay format, the recombinant proteins can be used in immunodot blot assay systems. The immunodot blot assay system uses a panel of purified recombinant polypeptides placed in an array on a nitrocellulose solid support. The prepared solid support is contacted with a sample and captures specific antibodies (specific binding member) to the recombinant protein (other specific binding member) to form specific binding member pairs. The captured antibodies are detected by reaction with an indicator reagent. Preferably, the conjugate specific reaction is quantified using a reflectance optics assembly within an instrument which has been described in U.S. patent application Ser. No. 07/227,408 filed Aug. 2, 1988. The related U.S. patent application Ser. No. 07/227,586 and 07/227.590 (both of which were filed on Aug. 2, 1988) further described specific methods and apparatus useful to perform an immunodot assay, as well as U.S. Pat. No. 5,075,077 (U.S. Ser. No. 07/227,272 filed Aug. 2, 1988). Briefly, a nitrocellulose-base test cartridge is treated with multiple antigenic polypeptides. Each polypeptide is contained within a specific reaction zone on the test cartridge. After all the antigenic polypeptides have been placed on the nitrocellulose, excess binding sites on the nitrocellulose are blocked. The test cartridge then is contacted with a test sample such that each antigenic polypeptide in each reaction zone will react if the test sample contains the appropriate antibody. After reaction, the test cartridge is washed and any antigen-antibody reactions are identified using suitable well-known reagents. As described in the patents and patent applications listed herein, the entire process is amenable to automation. The specifications of these applications related to the method and apparatus for performing an immunodot blot assay are incorporated herein by reference.

It also is within the scope of the present invention that fusion proteins prepared from the plasmid described herein can be used in assays which employ a first and second solid support, as follows, for detecting antibody to a specific antigen of an analyte in a test sample. In this assay format, a first aliquot of a test sample is contacted with a first solid support coated with recombinant protein specific for an analyte for a time and under conditions sufficient to form recombinant protein/analyte antibody complexes. Then, the complexes are contacted with an indicator reagent specific for the recombinant antigen. The indicator reagent is detected to determine the presence of antibody to the recombinant protein in the test sample. Following this, the presence of a different antigenic determinant of the same analyte is determined by contacting a second aliquot of a test sample with a second solid support coated with recombinant protein specific for the second antibody for a time and under conditions sufficient to form recombinant protein/second antibody complexes. The complexes are contacted with a second indicator reagent specific for the antibody of the complex. The signal is detected in order to determine the presence of antibody in the test sample, wherein the presence of antibody to either analyte recombinant protein, or both, indicates the presence of anti-analyte in the test sample. It also is contemplated that the solid supports can be tested simultaneously.

The use of haptens is known in the art. It is contemplated that haptens also can be used in assays employing fusion proteins produced by the plasmid of the invention in order to enhance performance of the assay.

The following examples are meant to illustrate, but not to limit, the spirit and scope of the invention.

EXAMPLES

Example 1

E2 Antigen Construction

Plasmid 577 was constructed by inserting coding sequence for a secretable HCV E2 antigen in two steps, as follows. First, a duplex synthetic oligonucleotide that had been digested with Spe 1 and Xba 1 was inserted into the Xba 1 cloning site of a previously constructed expression vector by sticky end ligation. This oligonucleotide contained sequence derived from rabbit immunoglobulin gamma chain peptide and other sequences included to create restriction sites for cloning purposes. It was then inserted downstream of a promoter element and RNA transcription start site. This DNA segment encoded amino acid sequences to be fused in frame at the Xba 1 sites to downstream gene sequences intended to be secreted from mammalian cells. The construction of this plasmid 577 is shown in FIG. 1. The sequence of this DNA segment is depicted in FIG. 2. A conceptual translation delineating the mammalian secretion signal peptidase cleavage site is shown in FIG. 3.

Second, a PCR product containing sequence derived from an HCV plasmid template was inserted as an Xba 1 fragment downstream of the rabbit heavy chain signal sequence. Encoded in the "upper" PCR primer sequence was an Xba 1 site, immediately followed by 12 nucleotide sequence that encoded the amino acid sequence Serine-Asparagine-Glutamic Acid-Leucine ("SNEL") the amino terminal sequence of human pro-urokinase. The amino acid sequence SNEL was intended to promote signal protease processing, efficient secretion and final product stability in culture fluids. This segment is underlined in FIG. 2. Immediately following this 12 nucleotide sequence the primer contained nucleotides complementary to template sequences encoding amino acids starting at aa 388 of HCV. The "lower" PCR primer contained sequences homologous to template sequences that encode amino acids ending at 664 of HCV, a duplicate stop codon, and an Xba 1 site for cloning purposes. E2 antigen was truncated at this position to promote secretion. The Xba 1 sites appear in large bold type face and the stop codons are underlined in FIG. 2.

The complete sequence of this inserted region is depicted in FIG. 2 and in SEQUENCE I.D. NO. 1. A graphical representation of this coding region is depicted in FIG. 1.

Referring to FIG. 1, plasmid 577 contains the following DNA segments described counterlockwise from the top of the plasmid, FIG. 1: (a) a 2.3 Kb fragment of pBR322 containing bacterial beta-lactamase and origin of DNA replication; (b) a 1.8 Kb cassette directing expression of a neomycin resistance gene under control of HSV-1 thyridine kinase promoter and poly-A addition signals; (c) a 1.9 Kb cassette directing expression of a dihydrofolate reductase gene under the control of an SV-40 promoter and poly-A addition signals; (d) a 3.5 Kb cassette directing expression of a modified hepatitis C virus derived gene under the control of the Simian Virus 40 T-ag promoter and transcription enhancer, the hepatitis B virus surface antigen enhancer I, and a fragment of Herpes Simplex Virus-1 genome providing poly-A addition signals; and (e) a residual 0.7 Kb fragment of Simian Virus 40 genome late region of no function of this plasmid. These data are summarized in TABLE 1 hereinabove. All of the segments of the vector were assembled by standard methods know to those skilled in the art of molecular biology.

Example 2

A. Transfection of Dihydrofolate Reductase Deficient Chinese Hamster Ovary Cells.

The plasmid 577 was transfected into CHO/dhfr cells (dxb-111) (Uriacio, et al., *Proc. Nat. Acad. Sci.* 77, 4451–4466 (1980); these cells are available from the American Type Culture Collection [A.T.C.C.], 12301 Parklawn Drive, Rockville, Md. 20852, under Accession No. CRL 9096), using the cationic liposome-mediated procedure (Felgner, P. L. et al., *Proc. Natl. Acad. Sci.* 84, 7413–7417 (1987), as follows. CHO/dhfr cells were cultured in Ham's F-12 media supplemented with 10% fetal calf serum, L-glutamine (1 μM) and freshly seeded into a 25 $cm^2$ flask at a density of 5–8×$10^5$ cells per flask twenty four hours prior to transfection. Fifteen micrograms of plasmid DNA was added to 1.5 mls of Opti-MEM I medium and 100 microliters of Lipofectin Reagent (Gibco-BRL, Grand Island N.Y.) was added to a second 1.5 ml portion of Opti-MEM I media. The two solutions were mixed and incubated at room temperature for 20 minutes. The culture medium was removed from cells and replaced with the Opti-MEM I-Lipofection-DNA solution for liposome-mediated transfection of DNA into cells in tissue culture. The cells were incubated for three hours at 37° C. after which the Opti-MEM I-Lipofectin-DNA solution was replaced with culture medium for an additional 24 hours prior to selection.

B. Selection and Amplification.

One day after transfection, cells were passaged 1:3 and incubated with dhfr/G418 selection medium (hereafter, "F-12 minus medium G"). Selection medium was Ham's F-12 with L-glutamine and without hypoxanthine, thymidine, and glycine (JRH Biosciences, Lenexa, Kans., USA ) and 300 micrograms per ml G418 (Gibco-BRL).

Colonies showing the presence of dihydrofolate reductase (Ringold, et al., *J. Mol Appl. Genet.* 1:165–174 (1981) plus aminoglycoside phosphotransferase (Southern, P. J. and Berg, P. J., *Mol. Appl. Genet.* 1:327–341 (1981) appeared after 4–5 days of incubation of transfected cells with F-12 minus medium G. After approximately two weeks, DHFR/G418 cells were sufficiently expanded to allow passage and continuous maintenance in F-12 minus medium G.

Amplification of the transfected UK-HCV-E2 gene was achieved by stepwise selection of $DHFR^+$, $G418^+$ cells with methotrexate (reviewed by Schimke, R., *Cell* 37, 705–713 (1984). Cells were incubated with F-12 minus medium G, containing 150 nM methotrexate (MTX), for approximately two weeks until resistant colonies appeared. The MTX resistant cells were passaged and maintained in the appropriate selection medium. Further amplification was achieved by selection with 5 μM MTX, and cells continuously maintained in the appropriate selection medium.

C. Maintenance and Storage of Cell Lines.

Cells in culture and undergoing various selection or amplification procedures were re-fed with the appropriate culture medium three times weekly. Cells were passaged 1:4, with appropriate medium, into 75 $cm^2$ flasks and incubated at 37° C. with 5% $CO_2$ using standard methods. Cryostorage was by resuspension of 2–4×$10^6$ cells in 1.8 ml of the appropriate culture medium containing 5% DMSO (Sigma Chem. Co., St. Louis, Mo., USA) and cold storage for 24 hours at −80° C. and then permanent storage at −135° C.

D. Antigen Production.

Ham's F12 custom minus medium was overlayed onto just confluent monolayers for 12 to 24 hours at 37° C. in 5% $CO_2$. Then, the growth medium was removed and the cells were rinsed three times with phosphate buffered saline (PBS) (with calcium and magnesium) available from Gibco-BRL, to remove the remaining media/serum which might be present. Cells then were incubated with VAS custom medium (VAS custom formulation with 1-glutamine with HEPES without phenol red, available from JRH Bioscience, product number 52-08678P), for one hour at 37° C. in 5% $CO_2$. As a final wash, the VAS then was discarded. Cells then were overlaid with VAS for production at 5 mls per T 25 $cm^2$ flask, scaled proportionally for larger flasks or roller bottles). For harvest 1, the medium is removed after three to four days of incubation and then frozen to await purification with harvests 2 and 3. The monolayers were overlayed with VAS for two more three to four day harvests. The cultures were observed daily to determine cell conditions.

E. Clarification and Concentration.

Harvests were clarified at 1500×g for 30 minutes. Supernatants were concentrated to 50× in an Amicon stirred cell equipped with an Amicon YM10 membrane (available from Amicon, Amicon, Beverly, Mass.).

Example 3

CHO-E2 Purification

The sialic acid containing CHO-E2 glycoprotein was purified to greater than 90% purity from cell supernatants by ion exchange and lectin chromatography. Ten (10) separate lots from two different protein-free media all were purified, which demonstrated the reproducibility and versatility of this procedure. Purity was evaluated by R-250 coomassie and silver staining. Theoretical molecular weight of 30 Kdal was verified by Endo-F digestion.

Supernatants from cells propagated in roller bottles were spun to remove cell debris and then concentrated using an Amicon YM10 membrane to 50× (50 ml). The 50× concentrate was final filtered through a 0.2 µm filter and then extensively dialyzed (12–14 Kdal cut-off) against S-Sepharose running buffer (0.02 M sodium phosphate, no salt, pH 6.5). The ion-exchange chromatography consisted of two columns (S-Sepharose and DEAE-Sepharose). Both columns were run in series, unwanted proteins were bound onto the columns while the protein of interest was contained in the flow. The ion exchange columns were cleaned to remove the unwanted proteins with 2 M NaCl in the columns' respective running buffer.

The concentrated and dialyzed supernatant first was loaded on an equilibrated S-Sepharose column (200 ml bed volume) at a flow rate of 5 ml/min. The unbound flow was collected, concentrated (YM10) to original volume and extensively dialyzed in DEAE-Sepharose running buffer (containing 0.02 M Tris buffer/0.1 M NaCl, pH 8.5). It was found that the conductivity of this buffer should be about 12 mS. After dialysis, the material was loaded onto a 200 ml DEAE-Sepharose column at a flow rate of 5 ml/min. The unbound flow was collected, concentrated (YM10) to original volume and extensively dialyzed in 0.01 M sodium phosphate, 0.13 M NaCl, pH 7.0. This buffer was termed the lectin WGA-Sepharose 6MB running buffer. Once the sample was changed into WGA running buffer, it was loaded at 0.5 ml/min onto a 10.0 ml WGA-Sepharose 6 MB column, collecting and recirculating the flow. After extensive washing (10 column volumes), the column flow was reversed and the purified CHO-E2 antigen was eluted using 10 mM N,N'-diacetylchitobiose in running buffer. The purified antigen was dialyzed against PBS and stored at −70° C.

Example 4

CHO-E2 Antigen Assay for Screening Cloned Cell Suspensions

A. Preparation of CHO-E2 Antigen Beads. Twenty microliters (20 µl) of cloned cell suspension or control suspensions (CHO cells transfected with expression vector containing no HCV insert) were placed into a microtiter well which was capable of containing a ¼ inch bead. The number of wells being tested was multiplied by 0.2 and by 1.05 to obtain the volume in milliliters (ml) of diluent necessary for coating. The diluent used was SMP diluent (available from Abbott Laboratories, Abbott Park, Ill.).

Two hundred microliters (200 µl) of the reagent obtained hereinabove was added to each well containing supernatant, sealed, and the tray containing the wells was placed in an incubator pre-warmed to 40° C. The trays were shaken in the Dynamic Incubator on Dynamic mode for 20 seconds in order to mix the samples. Following this, the trays were incubated for one hour at 40° C. in a static state. Then, the E2 peptide bead was added, covered and incubated for one hour at 40° C. in a static mode. Following this incubation, the trays were washed and 200 µl of conjugate was added per well (100 ng/ml of gamma spec G anti-human HRPO in HCV 2.0 conjugate diluent, list number 4A14C, available from Abbott Laboratories, Abbott Park, Ill.). This mixture was incubated at 40° C. in a static mode for 30 minutes. Following this incubation, the beads were washed and then transferred to an EIA tube box. Then, 300 µl of OPD substrate (available from bbott Laboratories, Abbott Park, Ill.) was added to each well and the resulting ixture was incubated for 30 minutes at 40° C. The reaction was stopped by adding 1.0 ml of 1 N $H_2SO_4$ per well. Each well was read at an absorbance of 492 ($A_{492}$) on an Abbott Quantum™ instrument, and the validity of the assay then was determined as follows:

Average $A_{492}$ of the negative control =1.000+/−0.10; the average $A_{492}$ of the positive control =0.025+/−0.10. Following these calculations, the percent reduction of the test sample was calculated as follows: (Average $A_{492}$ sample)+ 1×100=% Reduction Average $A_{492}$ Neg Control Example 5

Assays Utilizing E2 Antigen

Purified HCV E2 antigen prepared as described in the previous examples was coated onto polystyrene beads following methods well-known in the art at a concentration of 1.0 to 2.0 µg/ml. The components used in the coating procedure were adjusted to provide optimum sensitivity and specificity for the antibody assay test. The specificity of the E2 antibody assay was evaluated by testing specimens from populations of volunteer blood donors. All specimens were testd at 1:41 dilution in the enzyme immunoassay using goat anti-human IgG labeled with horseradish peroxidase as the signal generating compound according to the assay protocol hereinabove (see previous examples).

Chronic and acute non-A, non-B hepatitis (NANBH) specimens were obtained from multiple U.S. sites. Serially collected specimens from individuals seroconverting to HCV antigens were obtained from commercial plasma vendors. Archived samples which were HCV RNA positive (N=495) were obtained from a large virology reference laboratory in the U.S. without linkage to patients or donors. The RNA extraction and PCR amplification procedures have been described (D. Gretch et al., *J. Clin. Micro.* 30:2145–2149 (1992). Additional HCV RNA positive specimens were collected from Japan (C=59) and the Netherlands (N=33). Specimens from blood donors at risk for HCV infection (N=304) with ALT values greater than 100 IU/L were obtained from the New York Blood Center. Samples indeterminately reactive on Abbott MATRIX™ 1.0 HCV assay for HCV core antigen (N=139) and HCV NS3 antigen (N=149) were obtained from the Abbott Virology Reference Laboratory, North Chicago, Ill. A commerically available anti-HCV 2.0 positive blood donors and patients. A commerically available anti-HCV mixed titer panel (PHV 203) was obtained from Boston Biomedica, Inc. (BBI), West Bridgewater, MA. HCV 2.0 reactive plasma samples were obtained from North American Biologicals, Inc. (NABI) and only samples which were concordantly reactive in two HCV 2.0 EIA (available from Abbott Laboratories, Abbott Park, Ill. and Ortho Diagnostics, Inc., Raritan, N.J.) were analyzed further.

One hundred fifity nine (159) patients previously diagnosed with chronic NANBH were tested using the Abbott HCV 2.0 test and the E2 EIA. A total of 147/159 (92.5%) patients were positive with HCV 2.0 while 141/159 (88.5%) patients also had antibody to E2. Overall, there was 96.2% agreement between the HCV 2.0 and E2 assays. A high correlation (94%) between HCV core and E2 antibodies also was observed in this population. A similar high concordance was seen between HCV 2.0 and E2 assays in acute NANBH patients. Ninety-nine (99) of these 113 (87.6%) specimens gave concordant results (51 positive and 48 negative), while 10 specimens reacted exclusively with HCV 2.0 and 4 specimens were positive only in the E2 antibody assay. The overall reactive rates in acute patients for HCV 2.0 and the E2 EIA were 54% and 49%, respectively.

Serially collected specimens from 5 individual plasma donors who seroconverted to multiple HCV antigens were also shown to react wit the HCV E2 protein. In three of the five patients, E2 antibody was the first antibody detectable during seroconversion. Anti-E2 eventually appeared in all five cases.

A total of 587 individuals HCV RNA positive specimens were tested for antibody to E2 as well as for other individual HCV antibodies using the Abbott MATRIX™ HCV 2.0 assay. Five hundred seventy-one (571) of 587 of these RNA positive specimens werc shown to contain antibodies to E2, including 56/59 (94.9%) of the specimens collected in Japan. All E2 positive samples contained other HCV antibodies as detected by Abbott MATRIX™, but no single antibody occurred with greater frequency than E2 antibody in this population.

Among the cohort of blood donors with ALT values greater than 100 IU/L, 48 (15.8%) were positive for E2 antibodies. Forty-six (95.8%) of these 48 donors also were reactive in the Abbott HCV 2.0 EIA and were confirmed reactive in the Abbott MATRIX™ HCV 2.0 assay.

Specimens detected by Abbott MATRIX™ HCV 1.0 as having antibodies to HCV core or HCV NS3 exclusively, were tested for E2 antibodies. Fifty-nine (59) (42.4%) of 139 core reactive specimens were found to contain E2 antibodies as were 23/149 (15.4%) NS3 reactives.

A panel of well-characterized specimens with regard to serological markers was obtained from BBI and evaluated with the Abbott HCV 3.0 EIA and E2 antibody tests. HCV 2.0 EIA (Abbott and Ortho), HCV 3.0 EIA (Ortho), Abbott MATRIX™ HCV 1.0 and RIBA HCV 2.0 data were supplied by BBI with the panel. Eighteen (18) of 23 (78.3%) HCV 2.0 EIA positive (by both Abbott and Ortho assays) specimens were also anti-E2 positive. The two HCV negative panel members were E2 antibody negative.

Among the 23 HCV 2.0 concordantly positive specimens were six samples (26.1% of total) which scored negative in the Ortho HCV 3.0 EIA but remained reactive in the Abbott HCV 3.0 EIA. Three 50% of these six specimens were shown to contain antibodies to multiple HCV proteins including 2 specimens which had antibodies to E2. These two specimens were reactive to HCV core in both RIBA and Abbott MATRIX™ assays.

Thus, the E2 recombinant antigen from plasmid 577 was able to function in assays which employed it.

Other modifications and variations of the specific embodiments of the invention as set forth herein will be apparent to those skilled in the art. Accordingly, the invention is intended to be limited in accordance with the appended claims.

What is claimed is:

1. A method for detecting the presence of an anti-hepatitis C virus (HCV) antibody in a test sample comprising the following steps:
   (a) contacting at least one antigen specific for said antibody with a test sample under conditions that facilitate antigen/antibody complex formation, wherein said antigen is the recombinant glycosylated HCV protein encoded by plasmid 577 (p577) having the structure shown in FIG. 1 and has been isolated and purified from mammalian host cells transfected with p577; and
   (b) contacting the complex of step (a) with an indicator reagent comprising said antigen conjugated to an signal generating compound under conditions that facilitate antigen/antibody/indicator reagent complex formation, wherein the signal generated is an indication of the presence of said anti-HCV antibody in said test sample.

2. A test kit for the detection of hepatitis C virus (HCV)-specific antibody in a test sample, wherein said kit comprises at least one container containing an isolated and purified HCV antigen, said antigen consisting of the recombinant, glycosylated HCV protein encoded by the plasmid designated p577 having the structure shown in FIG. 1.

3. A composition comprising a recombinant, glycosylated hepatitis C virus (HCV) protein, wherein said protein is encoded by the plasmid designated p577 having the structure shown in FIG. 1 and said protein has been isolated and purified from mammalian host cells transfected with p577.

4. An isolated and purified plasmid encoding a recombinant, glycosylated hepatitis C virus (HCV) antigen, wherein said plasmid has the designation p577 and the structure set forth in FIG. 1.

* * * * *